United States Patent [19]

Martines et al.

[11] 4,100,190

[45] Jul. 11, 1978

[54] PRODUCTION OF PERCHLOROMETHYL MERCAPTAN

[75] Inventors: Vincent C. Martines, White Plains, N.Y.; Ramsey G. Campbell, Berkeley, Calif.

[73] Assignee: Stauffer Chemical Company, Westport, Conn.

[21] Appl. No.: 753,122

[22] Filed: Dec. 22, 1976

[51] Int. Cl.$^2$ .................. C07C 149/16; C07C 148/00
[52] U.S. Cl. ................................................. 260/543 H
[58] Field of Search ................................... 260/543 H

[56] References Cited

U.S. PATENT DOCUMENTS

| | | | |
|---|---|---|---|
| 2,545,285 | 3/1951 | Kamlet | 260/543 H |
| 2,575,290 | 11/1951 | Ohsol et al. | 260/543 H |
| 2,647,143 | 7/1953 | Pitt et al. | 260/543 H |
| 2,666,081 | 1/1954 | Churchill | 260/543 H |
| 2,759,969 | 8/1956 | Jonas | 260/543 H |
| 3,014,071 | 12/1961 | Hoyt et al. | 260/543 H |
| 3,673,246 | 6/1972 | Meyer et al. | 260/543 H |
| 3,808,270 | 4/1974 | Rupp et al. | 260/543 H |
| 3,878,243 | 4/1975 | Zupancic | 260/543 H |
| 3,968,155 | 7/1976 | Gueren | 260/543 H |
| 3,993,693 | 11/1976 | Bhutane | 260/543 H |

FOREIGN PATENT DOCUMENTS

| | | | |
|---|---|---|---|
| 508,163 | 12/1954 | Canada | 260/543 H |
| 1,437,908 | 3/1966 | France | 260/543 H |

OTHER PUBLICATIONS

Soznovsky, "Chem. Rev." vol. 58, pp. 509–512 (1958).

*Primary Examiner*—Norman Morgenstern
*Attorney, Agent, or Firm*—Roger S. Benjamin

[57] ABSTRACT

A method for improving the yield of perchloromethyl mercaptan by including with the reaction mixture phosphates or phosphites in amounts effective to suppress the formation of undesirable byproducts, such as carbon tetrachloride and sulfur monochloride.

7 Claims, No Drawings

PRODUCTION OF PERCHLOROMETHYL MERCAPTAN

BACKGROUND OF THE INVENTION

This invention relates to improvements in the production of perchloromethyl mercaptan. More particularly, it relates to the use of phosphates and/or phosphites as additives which serve to improve the yield of perchloromethyl mercaptan.

Perchloromethyl mercaptan, $Cl_3CSCl$, also known as trichloromethane sulfenyl chloride, has commercial importance as an intermediate in the manufacture of fungicides, bactericides, germicides, herbicides, soil fumigants and pharmaceuticals.

Perchloromethyl mercaptan was first described in a production scheme by Rathke in Annalen, Volume 167, at page 195 (1873). Rathke's method, which is still in use today, utilizes an iodine catalyst. The reaction scheme operates most efficiently at temperatures below about 40° C., in accordance with the following equations:

$$CS_2 + 3Cl_2 \rightarrow CCl_3SCl + SCl_2 \quad (1)$$

$$2CS_2 + 5Cl_2 \rightarrow 2CCl_3SCl + S_2Cl_2 \quad (2)$$

$$CS_2 + 3Cl_2 \rightarrow CCl_4 + S_2Cl_2 \quad (3)$$

In addition to sulfur dichloride, sulfur chloride (also known as sulfur monochloride) and carbon tetrachloride, the reaction can also form other compounds as unwanted byproducts. Although more volatile byproducts such as carbon tetrachloride and sulfur dichloride can be removed from the reaction mixture by distillation, it is extremely difficult to separate perchloromethyl mercaptan from sulfur chloride by this method. This is due to the fact that the boiling points of perchloromethyl mercaptan and sulfur chloride are very close to each other.

The prior art has proposed several methods for improving the basic Rathke method. For example, U.S. Pat. No. 3,544,625 to Masat, discloses a method for producing perchloromethyl mercaptan by chlorinating carbon disulfide in the presence of a solution of inorganic acids, such as hydrochloric acid. U.S. Pat. No. 3,673,246 to Meyer et al, discloses a continuous process for producing perchloromethyl mercaptan wherein carbon disulfide is reacted with chlorine on or in intimate contact with activated carbon at temperatures of about −5° to +100° C. U.S. Pat. No. 3,808,270 to Rupp et al, discloses a continuous process for producing perchloromethyl mercaptan by reacting carbon disulfide and chlorine in a reaction zone filled with granular active carbon completely immersed in the liquid reaction mixture while maintaining temperatures in the range of about 40° to about 135° C. U.S. Pat. No. 3,878,243 to Zupancic discloses a homogeneous catalyst system comprising a lead salt of a carboxylic acid which is soluble in carbon disulfide.

Notwithstanding the effectiveness of the above prior art patents as methods for producing perchloromethyl mercaptan (PMM), they do not deal with preventing the tendency of PMM to react with chlorine or sulfur dichloride to form carbon tetrachloride, sulfur, and sulfur monochloride. Mixtures of carbon disulfide, sulfur dichloride and perchloromethyl mercaptan also react in a similar fashion. The reactions which form carbon tetrachloride are believed to be accelerated by trace amounts of metals, such as iron, tin, and bronze, in the reaction mixture.

Small quantities of iron are generally present in the commercial carbon disulfide and chlorine used as reactants for PMM, at levels on the order of parts per million. The chlorine can be treated by passing it through a glass wool filter to remove most of the iron. However, the presence of iron at levels as low as one part per million can be deleterious and capable of effecting significant reductions in the yield of perchloromethyl mercaptan. It has, therefore, been an objective of industry to develop agents capable of ameliorating the effect of metallic impurities present in the reactants and/or catalyst, so that the formation of carbon tetrachloride, sulfur chloride, and other undesirable byproducts is suppressed.

Another problem in the production of perchloromethyl mercaptan occurs in the decomposition of sulfur dichloride to sulfur chloride and chlorine in the following manner:

$$2SCl_2 \rightleftharpoons S_2Cl_2 + Cl_2 \quad (4)$$

This reaction is undesirable due to the fact that the boiling points of perchloromethyl mercaptan and sulfur chloride are so close to each other that it is impractical to separate them by distillation. Thus, it has also been an objective of industry to develop agents for stabilizing sulfur dichloride to thereby prevent it from forming sulfur chloride and chlorine.

The present invention has achieved improvements in the production of perchloromethyl mercaptan via the use of phosphates and/or phosphites as additives which are believed to suppress the formation of the undesirable byproducts occurring in reactions (3) and (4).

Description of the Preferred Embodiment

In accordance with the present invention, improved yields of perchloromethyl mercaptan have been achieved by the addition of small amounts of phosphates and/or phosphites to the reaction system.

The phosphates and phosphites that have been found to be most effective in accomplishing the purposes of the present invention have the following respective structural formulae:

(A)

(B)

wherein R, R' and R" independently can be hydrogen, hydrocarbyl, or substituted hydrocarbyl, however, R, R' and R" cannot all be hydrogen simultaneously.

Typical examples of hydrocarbyl groups are alkyl, aralkyl, alkaryl, and aryl, with the alkyl groups having from 1 to about 20 carbon atoms, and preferably from 1 to about 10 carbon atoms. The alkyl groups can be straight, branch chained or cyclic.

Typical examples of substituted alkyl and substituted aryl as used herein are meant to designate alkyl or aryl groups having attached thereto at least one substituent of the type: halogen, cyano, carboxyl, carboxylate, amido, amino, nitro, hydroxy or alkoxy, with the proviso that the substituents not adversely affect the preparation of perchloromethyl mercaptan. The preferred substituents are halogen, and most preferably, chlorine.

A typical aryl group can be phenyl and the like. Alkaryl groups can be cresyl, xylyl and the like. Aralkyl can be benzyl and the like.

Typical examples of the preferred phosphates and/or phosphites found to be especially effective in increasing the yield of perchloromethyl mercaptan have alkyl and substituted alkyl groups of from about 4 to about 10 carbon atoms.

The addition of the phosphates and/or phosphites to the reactants involved in the production of perchloromethyl mercaptan is accomplished most effectively by contacting the additives in situ with carbon disulfide and a catalyst. It is to be noted that the catalyst chosen must be inert to the additives, otherwise the reaction will cease. Thus, for example, the phosphate and/or phosphite additives of the present invention will not function with an iodine catalyst. Activated carbon as a catalyst is most effective in utilizing the additives of the present invention. Chlorine is then contacted with the reaction mixture over an extended period of time while maintaining the reaction temperature in accordance with the particular catalyst system utilized, and mode of production for the PMM.

It should be noted that the reaction temperatures required for batch process production of PMM are generally lower than the temperatures which can be maintained in a continuous process. For example, batch process temperatures generally vary from about 10° to about 40° C., when using a carbon catalyst. At above about 40° C. in a batch process, PMM would tend to decompose into $CCl_4$ and $S_2Cl_2$. The carbon catalyzed system can operate in a continuous mode at temperatures above 40° C. if done in accordance with U.S. Pat. No. 3,808,270.

The phosphates and/or phosphites are generally added in amounts which vary from about 0.01 to about 10%, and preferably from about 0.1 to about 5% by weight of the carbon disulfide feed. Larger amounts can be used, however, no advantage is accrued thereby. In general, it has been found that use of phosphates and/or phosphites in the stated manner significantly reduces the formation of carbon tetrachloride and other unwanted byproducts, and increases the yield of perchloromethyl mercaptan to yields higher than 95%, based upon the chlorine reacted.

It should be noted that although the phosphate and/or phosphite additives are not to be used in catalyst systems which can interreact with these additives, the phosphate and/or phosphite additives can be used to stabilize the crude perchloromethyl mercaptan product and act to prevent sulfur dichloride from reacting to form sulfur chloride and chlorine.

In the examples which follow, all parts and percentages are by weight unless otherwise specified.

EXAMPLE 1 (Continuous Reaction)

A 1-½ inches I.D. glass tube was filled to a height of 30 inches with 8-12 mesh size granular activated carbon (CXAL coconut charcoal from Union Carbide). The glass reactor was fitted with a top inlet for $CS_2$ feed and a bottom inlet for $Cl_2$ as well as a botton drain for collecting the crude product. A reflux condenser was fitted to the vapor outlet of the column in order to avoid the loss of $CS_2$. $CS_2$ was added to the reactor in an amount sufficient to cover the catalyst bed. $Cl_2$ was then metered to the reactor until about 90% of the $CS_2$ had been reacted (by gas liquid chromatographic analysis). $Cl_2$ and $CS_2$ were then fed to the reactor simultaneously in the ratio of 3 moles $Cl_2$/mole $CS_2$. Crude PMM was withdrawn from the bottom of the reactor at a rate such that the liquid level in the reactor was maintained at the top of the catalyst bed. The maximum temperature in the reactor was kept at less than or equal to 110° C. by limiting the $CS_2$ feed rate to about 0.16 gm. $CS_2$/gm. catalyst per hour.

This run was then repeated exactly except for the addition of 3% weight (based on $CS_2$) tributyl phosphate (TBF) to the $CS_2$ with the following results.

| | Without TBF | With 3% TBF |
|---|---|---|
| % $CS_2$ conversion | 98.0 | 98.2 |
| % Selectivity for PMM | 78.8 | 96.4 |
| % Selectivity for $CCl_4$ | 21.2 | 3.6 |
| % $S_2Cl_2$ in distilled product | 11.0 | 2.4 |
| % PPM yield on $CS_2$ | 77.2 | 94.7 |
| % $CCl_4$ yield on $CS_2$ | 20.8 | 3.5 |

EXAMPLES 2-4

76 grams of carbon disulfide (1 mole), 30 grams of activated carbon (CXAL coconut charcoal from Union Carbide) and 0.38 grams of tributoxyethylphosphate were placed into a 250 ml. glass jacketed flask fitted with a chlorine inlet tube, dry ice condenser and mechanical stirrer. Thermostated water at a temperature of 35° C. was continuously cycled through the jacket. The solution was stirred and 182.9 grams of chlorine were bubbled through the solution over a 4 hour period. A total of 247 grams of liquid residue was recovered from the jacketed flask after separation from the charcoal. This material was analyzed by gas liquid chromatography (glc). The results are shown in the Table below. The above procedure was repeated except for different additives, with the results shown in the Table.

TABLE

| Example | Additive | PMM Yield, %[1] | % $CCl_4$ |
|---|---|---|---|
| 2 | Tributoxyethyl phosphate $(C_4H_9OCH_2CH_2O)_3P=O$ | 95 | 5 |
| 3 | Tris(betachloroethyl)-phosphate $(ClCH_2CH_2O)_3P=O$ | 99.3 | 0.7 |
| 4 | Dibutyl acid phosphate[2] $(C_4H_9O)_2\overset{\overset{O}{\|}}{P}-OH$ | 99.8 | 0.2 |

[1]All yields based upon $Cl_2$ consumed, analysis by glc
[2]Charcoal was washed with HCl, then neutralized

What is claimed is:
1. In a method for producing perchloromethyl mercaptan via the catalytic reaction of chlorine and carbon disulfide, the improvement which comprises contacting the reactants with additive selected from the group consisting of phosphates, phosphites, or blends thereof, said phosphates having the following structure:

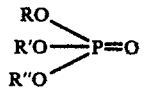

wherein R, R' and R" independently are hydrogen, hydrocarbyl, or substituted hydrocarbyl, however, R, R' and R" cannot all be hydrogen simultaneously, and said phosphites having the following structure:

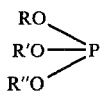

wherein R, R' and R" independently are hydrogen, hydrocarbyl, or substituted hydrocarbyl, however, R, R' and R" cannot all be hydrogen simultaneously, said additive being contacted with said reactants in amounts effective to suppress the formation of carbon tetrachloride and sulfur monochloride.

2. The method of claim 1, wherein the additive consists of phosphates having the following structure:

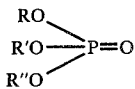

wherein R, R' and R" independently are hydrogen, hydrocarbyl, or substituted hydrocarbyl, however, R, R' and R" cannot all be hydrogen simultaneously.

3. The method of claim 1 wherein said phosphates and/or phosphites are alkyl and contain from 1 to about 10 carbon atoms.

4. The method of claim 1 wherein said phosphates and/or phosphites are added in amounts which vary from about 0.01 to about 10% by weight of the carbon disulfide feed.

5. The method of claim 4 wherein said phosphates and/or phosphites vary from about 0.1 to about 5% by weight of the carbon disulfide feed.

6. The method of claim 1 wherein said catalyst is activated carbon.

7. In a method for producing perchloromethyl mercaptan via the catalytic reaction of chlorine and carbon disulfide, the improvement which comprises:
   (1) using an activated-carbon catalyst, and
   (2) contacting the reactants with additives selected from the group consisting of tributyl phosphate, tributoxyethyl phosphate, tris(betachloroethyl)-phosphate, and dibutyl acid phosphate, said additives being contacted with said reactants in amounts effective to suppress the formation of carbon tetrachloride and sulfur monochloride.

* * * * *

UNITED STATES PATENT AND TRADEMARK OFFICE
CERTIFICATE OF CORRECTION

PATENT NO. : 4,100,190
DATED : July 11, 1978
INVENTOR(S) : Vincent C. Martines and Ramsey G. Campbell It is certified that error appears in the above-identified patent and that said Letters Patent are hereby corrected as shown below:

Column 3, Line 65, after the symbol, $Cl_2$, insert the word, -- feed --;

Column 4, Line 22, change "PPM" to -- PMM --.

Signed and Sealed this

Twenty-fourth Day of April 1979

[SEAL]

Attest:

RUTH C. MASON
*Attesting Officer*

DONALD W. BANNER
*Commissioner of Patents and Trademarks*